United States Patent [19]

Den Boer et al.

[11] Patent Number: 4,652,313

[45] Date of Patent: Mar. 24, 1987

[54] AQUEOUS LAKE PIGMENT SUSPENSION

[75] Inventors: Patrick Den Boer, Glen Rock; Richard F. Heinze, Bridgewater, both of N.J.; Benjamin L. Meyers, Highland Mills, N.Y.; Barendra C. Mallik, Fair Lawn, N.J.

[73] Assignee: Crompton and Knowles Corporation, New York, N.Y.

[21] Appl. No.: 664,320

[22] Filed: Oct. 24, 1984

[51] Int. Cl.$^4$ .............................................. C09D 3/10
[52] U.S. Cl. ...................................... 106/289; 106/23; 106/25; 106/308 C; 106/137; 106/208; 106/209; 424/474
[58] Field of Search ..................... 106/289, 23, 308 C, 106/308 F, 208, 27, 209, 137, 25; 424/34, 35, 36

[56] References Cited

U.S. PATENT DOCUMENTS

| | | | |
|---|---|---|---|
| 2,954,323 | 9/1960 | Endicott et al. | 424/33 |
| 3,028,349 | 4/1962 | Rowland et al. | 106/237 |
| 3,576,663 | 4/1971 | Signorino et al. | 428/478.2 |
| 3,694,237 | 9/1972 | Piotrowski | 424/34 |
| 3,981,984 | 9/1976 | Signorino | 424/33 |
| 3,992,215 | 11/1976 | Su et al. | 106/308 F |
| 4,154,622 | 5/1979 | Momoi et al. | 106/308 F |
| 4,197,221 | 4/1980 | Eisenmenger et al. | 106/308 F |
| 4,301,020 | 11/1981 | Johnson, Jr. et al. | 106/308 F |
| 4,497,847 | 2/1985 | Kurihara et al. | 424/35 |
| 4,525,345 | 6/1985 | Dunn et al. | 424/35 |

Primary Examiner—Amelia B. Yarbrough

[57] ABSTRACT

This invention relates to a pigment suspension usable for film coating tablets and the like, comprising lake pigment particles, a polymeric colloid, a viscosity lowering agent, which permits a higher concentration of pigment particles in the pigment suspension, and an aqueous solvent. A typical pigment suspension comprises a lake pigment, titanium dioxide, a natural gum, sodium tartrate, and water.

23 Claims, No Drawings

AQUEOUS LAKE PIGMENT SUSPENSION

THE BACKGROUND OF THE INVENTION

Pigment suspensions are used for producing coating suspensions for coating such items as pharmaceutical tablets or pills, confectionary pieces, and the like. The pigment suspension is typically stirred into a larger volume of solution to produce a coating suspension which is used in the coating process. One process of coating is generally known as film coating in which the coating solution includes a film forming polymer. U.S. Pat. No. 2,954,323 to Endicott et al. discloses examples of film coating. Another technique, frequently used, with respect to confectionary pieces, is generally known as sugar coating, in which the pigment suspension is added to a sugar syrup solution of Sugar and water.

Pigment suspensions for use in making coating suspensions are preferably sold having a concentration of pigment as high as possible. However, as the concentration of pigment increases, the suspension becomes more viscous and tends to reach a point where it becomes difficult to pour from its container. Over time, a thick suspension of pigment may even harden to the extent of becoming unusable.

In developing a high concentration pigment suspension, it is desirable to obtain a product in which the pigment particles form a stable suspension and will not settle. The need is for a pigment suspension which will readily pour from its container and will maintain its uniform properties during both transportation and storage, until ready for application in a coating suspension. U.S. Pat. No. 3,981,984 to Signorino discloses a pigment suspension which claims to achieve a high concentration of pigment in a non-aqueous solvent. The pigment supension consists of pigment particles, a protective colloid such as hydroxypropyl cellulose, and a non-aqueous solvent such as ethanol. Signorino discloses that as the pigment particles are added to the solvent, the mixture becomes too viscous, and the further addition of the protective colloid serves to suspend the particles and reduce the viscosity.

In view of the increasingly strict requirements of governmental regulating agencies in regard to the use of organic solvents, it has become desirable to obtain an aqueous pigment suspension. A high content of pigment is not normally possible and the present invention involved a search for a combination of ingredients which would permit a high content of pigment particles in an aqueous suspension. However, the invention is also applicable to suspensions in organic solvents which include a sufficient amount of water to dissolve what is referred to below as the viscosity reducing agent.

THE OBJECTS OF THE INVENTION

One object of the present invention is to achieve a pigment suspension which contains a high pigment content.

Another object of the present invention is to achieve a high concentration pigment suspension in an aqueous solvent or a mixture of water and an organic solvent.

A further object of the invention is to obtain a high concentration pigment suspension which pours readily from its container.

A further object of the invention is to obtain a high concentration pigment suspension which does not settle upon standing.

A further object of the present invention is to obtain a pigment suspension with a high pigment concentration which is capable of being transported to customers in containers, and which may readily be combined with a film-forming polymer solution or sugar solution by stirring.

The above and other objects of the present invention will become apparent from a reading of the following detailed description of the invention and the preferred embodiments thereof.

DETAILED DESCRIPTION OF THE INVENTION

The pigment suspension of the present invention comprises a mixture of a pigment, a polymeric colloid, a viscosity lowering agent, and water.

The pigments suitable for use in the context of the present invention include FD&C lakes, which are dyes combined with a metal hydroxide substratum. A variety of lakes, including lakes incorporating azo, triphenylmethane, fluorescein, and sulfonated indigo dyes, are suitable in the present invention. FD&C lakes are suitable for application in food, drug, and cosmetic products.

Lakes have been developed with a wide range of strengths. For food and confection applications, the mid-range dye content lakes are the most useful. These lakes are available from several sources. Suitable lakes are manufactured by Warner-Jenkinson Manufacturing Company of Saint Louis, Mo. (hereinafter referred to as "W-J"), and Crompton & Knowles Corporation of Fairlawn, N.J. (hereinafter referred to as "C&K"). For example, the following pigments are commercially available from C&K and W-J:

Yellow #6/40%
Yellow #5/36%
Blue #1/11%
Blue #2/39%
Red #40/40%
Red #27/36%
Red #3/40%

It has been found that due to variations in the processes of manufacturing lakes, the properties of a particular brand of lake, produced by one manufacturer, may not be as satisfactory in the present invention as that produced by another manufacturer.

For example, it has been found that for use in the present invention, Blue #2/39% pigment as presently manufactured by W-J is preferable. Similarly, it has been found that for use in the present invention, Blue #1/11% pigment, as presently manufactured by C&K, is preferable.

A 50/50 combination of C&K and W-J lakes may be preferable. In general, it was found that W-J lakes tend to have a higher tint, but may cause thickening. By using a mixture of W-J and C&K lakes, both a high tint and non-thickening is more readily obtained. Of course, developments and changes in the lakes by their manufacturers may require a reassessment, as would be capable by those skilled in the art, of the properties of a particular brand in regard to use in the present invention.

In each individual case of a particular lake, it is readily determined by trial and error.

The concentration of pigment in the pigment suspension by weight is in the range of 20% to 75%. Preferably a range of 25% to 65% is obtained. Most preferably a range of 30% to 60% is obtained. However, the amount of pigment achieved in any particular suspension depends to some degree on the particular pigment used and, somewhat higher contents of one particular pigment or a particular brand of pigment may be achieved than with another.

The polymeric colloid assists in preventing settling and hardening of the pigment Gums, both natural and synthetic, have been found to be suitable polymeric colloids. Suitable gums include, but are not limited to, gum arabic, quar gum, agar, xantham gum, PG alginate, hydroxypropyl cellulose, gum trag, Gelatin 250 Bloom, citrus pectin, and carrageenan. Preferable gums include gum arabic, xanthan gum and quar gum. The most preferable polymeric colloid is xanthan gum. In substitution of gum, such polymeric colloids as corn starch or polyvinylpyrrolidone may also be employed.

The polymeric colloid is present in the invention in amounts, by weight, ranging from 0.005 to 5.0 percent. As is evident, only relatively very small quantities of the polymeric colloid need be present in the suspension. A preferred range is 0.01 to 2.0 percent and most preferably 0.05 to 0.50 percent.

The viscosity lowering agent is a salt of an organic, carboxyl containing compound and mixtures thereof with the acid form. Preferred viscosity lowering agents include salts of compounds having one to three carboxylic groups. In addition, it has been found that lactones, which are believed to convert to carboxy containing compounds in water, are also suitable. Viscosity lowering agents include, but are not limited to, salts of adipic acid, benzoic acid, citric acid, fumaric acid, succinic acid, maleic acid, lactic acid, tartaric acid, and propionic acid and mixtures with the acid thereof. In addition such lactones as ascorbic acid and glucono-delta lactone may also be employed.

The viscosity lowering agents should, at least partly, be in the salt form. A 50/50 combination of the salt and acid is suitable. For example, sodium citrate, by itself, or a mixture of sodium citrate and citric acid, produces excellent results. On the other hand citric acid, by itself, did not work as well. It is surmised that the viscosity lowering agent complexes or chelates to the lake pigment particles. Due to the wide variety of dyes present in lake pigments, it is further surmised that the metal hydroxide substrate of the FD&C lakes functions in the complexing of the viscosity lowering agent. The resulting complex is believed to have electronic properties such that they repel another such complex, thereby resulting in dispersed pigment particles which form a thin, less viscous suspension, preventing thickening and hardening thereof.

The complexing or chelating effect is surmised, based partly on the fact that a similar effect is not acheived by a mere acid. For example, hydrochloric acid does not work, and the acid form alone of the given viscosity lowering agents are either inferior or unsatisfactory to the salt form of the viscosity lowering agents.

The presence of one of the viscosity lowering agents can result in a dramatic lowering of the viscosity of the suspension. Consequently, good flowability of the suspension is obtained. The suspension can be readily poured from its container and it neither unduly thickens nor settles. The viscosity lowering agent is present in an amount of 0.005 to 5 percent by weight in the mixture. Preferably, the agent is present in an amount of 0.005 to 2 percent and most preferably about 0.01 to 0.50 percent. In many cases, even a relatively very small amount of agent can drastically and favorably effect the properties of the suspension.

The above described components are dispersed in an aqueous solvent. The amount of water is suitably as high as 60 to 80 percent, depending on the amount of pigment. As described in greater detail below, organic solvents may also be included, in which case the amount of water may suitably be in the range of 5 to 30 percent.

The compositions were tested by what is referred to as an oven test. An oven test is an accelerated method of assessing the long-term properties of a pigment suspension. The oven test typically involved heating the pigment suspension at 104° F. for a period of 96 hours. This acelerated test is believed to be equivalent to 3 to 4 months at 85° F. The oven test results were evaluated according to the following rating system.

| Rating | RATING SYSTEM Description |
|---|---|
| 1 | A rock hard or very hard settle is obtained. The suspension fails to redisperse. |
| 2 | A paste or semi-hard solid is obtained. The suspension fails to pour from its container without force or requires the use of a spatula. |
| 3 | A threshold suspension, with some supernatant, is obtained. After agitation, the suspension is still thick, but pourable. |
| 4 | A suspension with or without supernatant but no settle is obtained. The consistency is like thick yogurt or jam. On agitation the suspension becomes fluid. |
| 5 | A soft, fluid dispersion with no settle is obtained. It pours from its container with no agitation and flows freely. |
| 5.5 | The suspension has no settle, but is very watery. |
| 6 | The suspension is too watery, and is not acceptable. |

The following examples are intended to illustrate the present invention.

EXAMPLE 1

In a blender, the following components were weighed out and mixed:

| Component | Percent by Weight |
|---|---|
| Distilled Water | 69.93 |
| Xanthan Gum | 0.02 |
| TiO$_2$ 3328 | 15.00 |
| Yellow #6/40% | 15.00 |
| Sodium Citrate | 0.05 |

After a period of 96 hours at 104° F., the pigment suspension exhibited a rating of 5.0.

This example, with 0.05% sodium citrate, was repeated except with increasing percentages by weight of sodium citrate. Pigment suspension with 0.10, 0.15, 0.20, and 0.50% of sodium citrate were obtained. The most preferred pigment suspensions were obtained with 0.05, 0.10, and 0.15 percent citrate. A rating of 5.0 or 5.5 was exhibited by each of such suspensions. The solutions with 0.20 and 0.50 percent sodium citrate tended to be more watery than optimally desirable. For example, after a period of 96 hours at 104° F., a rating of 6 was exhibited by the suspension having 0.50 percent sodium citrate.

EXAMPLE 2

In a blender, the following components were weighed out and mixed:

| Component | Percent by Weight |
|---|---|
| Distilled Water | 69.90 |
| Xanthan Gum CVF | 0.50 |
| TiO$_2$ 3328 | 15.00 |
| Yellow #6/40% | 15.00 |
| Sodium Citrate | 0.05 |

After 4 days at 104° F., the suspension exhibited a rating of 5.0.

The above formula was repeated at increasing percentages of sodium citrate and, rather that 0.05 percent, percentages of 0.10, 0.15, 0.20, and 0.50 were tested.

The most preferred amounts of sodium citrate in the above formula were found to be by weight 0.05% and 0.10%, each exhibiting, respectively, a rating of 5.0 and 5.5. At high percentages, a rating of 6 was obtained after 4 days at 104° F. Therefore, increasing the amount of sodium citrate above an optimal amount of sodium citrate tended to result in a more watery suspension than desirable.

Further examples shown in Table A to Table G, below illustrate the effect of changing the amount of gum and sodium citrate in the pigment suspension.

TABLE A

Percentage Weight

| COMPONENT | Trial 1 | 2 | 3 | 4 | 5 | 6 | 7 | 8 | 9 | 10 |
|---|---|---|---|---|---|---|---|---|---|---|
| Distilled Water | 69.80 | 69.75 | 69.70 | 69.40 | 69.50 | 69.45 | 69.40 | 69.35 | 69.30 | 69.00 |
| Gum Xanthan | 0.10 | 0.10 | 0.10 | 0.10 | 0.50 | 0.50 | 0.50 | 0.50 | 0.50 | 0.50 |
| TiO$_2$ 3328 | 15.00 | 15.00 | 15.00 | 15.00 | 15.00 | 15.00 | 15.00 | 15.00 | 15.00 | 15.00 |
| Yellow #6/40 AC7326 | 15.00 | 15.00 | 15.00 | 15.00 | 15.00 | 15.00 | 15.00 | 15.00 | 15.00 | 15.00 |
| Sodium Citrate | 0.10 | 0.15 | 0.20 | 0.50 | — | 0.05 | 0.10 | 0.15 | 0.20 | 0.50 |
| Total Percentage | 100 | 100 | 100 | 100 | 100 | 100 | 100 | 100 | 100 | 100 |
| Rating After 96 hrs. | 4.5 | 6.0 | 6.0* | 6.0* | 2.0* | 2.0* | 3.0* | 3.5 | 3.5 | 4.0 |
| Rating after 8 days | 5.5 | 5.5 | — | — | — | — | — | 3.0 | 3.5 | 4.5 |

*Denotes the sample was discarded after the 1st observation.

TABLE B

Percentage Weight

| COMPONENT | Trial 1 | 2 | 3 | 4 | 5 | 6 | 7 | 8 | 9 | 10 | 11 | 12 |
|---|---|---|---|---|---|---|---|---|---|---|---|---|
| Distilled Water | 69.98 | 69.93 | 69.88 | 69.83 | 69.38 | 69.48 | 69.95 | 69.90 | 69.85 | 69.80 | 69.75 | 69.45 |
| Gum Xanthan | 0.02 | 0.02 | 0.02 | 0.02 | 0.02 | 0.02 | 0.05 | 0.05 | 0.05 | 0.05 | 0.05 | 0.05 |
| TiO$_2$ 3328 | 15.00 | 15.00 | 15.00 | 15.00 | 15.00 | 15.00 | 15.00 | 15.00 | 15.00 | 15.00 | 15.00 | 15.00 |
| Yellow #6/40 AC5617 | 15.00 | 15.00 | 15.00 | 15.00 | 15.00 | 15.00 | 15.00 | 15.00 | 15.00 | 15.00 | 15.00 | 15.00 |
| Sodium Citrate | — | 0.05 | 0.10 | 0.15 | 0.20 | 0.50 | — | 0.05 | 0.10 | 0.15 | 0.20 | 0.25 |
| Total Percentage | 100 | 100 | 100 | 100 | 100 | 100 | 100 | 100 | 100 | 100 | 100 | 100 |
| Rating after 96 hrs. | 1.0* | 2.0* | 2.5* | 3.5 | 4.0 | 5.5 | 1.0* | 1.0* | 1.5* | 3.5 | 4.0 | 5.5 |
| Rating after 8 days | — | — | — | 2.0 | 3.0 | 5.5 | — | — | — | 1.0 | 3.0 | 5.5 |

| COMPONENTS | Trial 13 | 14 | 15 | 16 | 17 | 18 | 19 | 20 | 21 | 22 | 23 | 24 |
|---|---|---|---|---|---|---|---|---|---|---|---|---|
| Distilled Water | 69.90 | 69.85 | 69.80 | 69.75 | 69.70 | 69.40 | 69.50 | 69.45 | 69.40 | 69.35 | 69.30 | 69.00 |
| Gum Xanthan | 0.10 | 0.10 | 0.10 | 0.10 | 0.10 | 0.10 | 0.50 | 0.50 | 0.50 | 0.50 | 0.50 | 0.50 |
| TiO$_2$ 3328 | 15.00 | 15.00 | 15.00 | 15.00 | 15.00 | 15.00 | 15.00 | 15.00 | 15.00 | 15.00 | 15.00 | 15.00 |
| Yellow #6/40 AC 5617 | 15.00 | 15.00 | 15.00 | 15.00 | 15.00 | 15.00 | 15.00 | 15.00 | 15.00 | 15.00 | 15.00 | 15.00 |
| Sodium Citrate | — | 0.05 | 0.10 | 0.15 | 0.20 | 0.50 | — | 0.05 | 0.10 | 0.15 | 0.20 | 0.50 |
| Total Percentage | 100 | 100 | 100 | 100 | 100 | 100 | 100 | 100 | 100 | 100 | 100 | 100 |
| Rating after 96 hrs. | 1.0* | 1.0* | 1.0* | 2.0* | 4.5 | 5.5 | 1.0* | 1.0* | 1.0* | 1.0* | 2.0* | 5.0 |
| Rating after 7 days | — | — | — | — | 2.0 | 5.5 | — | — | — | — | — | 5.0 |

*Denotes the sample was discarded after the 1st observation.

TABLE C

Percentage Weight

| COMPONENTS | 1 | 2 | 3 | 4 | 5 | 6 | 7 | 8 | 9 | 10 | 11 | 12 |
|---|---|---|---|---|---|---|---|---|---|---|---|---|
| Distilled Water | 69.98 | 69.93 | 69.88 | 69.83 | 69.78 | 60.48 | 69.95 | 69.90 | 69.85 | 69.80 | 69.75 | 69.45 |
| Gum Xanthan 0.02 | 0.02 | 0.02 | 0.02 | 0.02 | 0.02 | 0.02 | 0.05 | 0.05 | 0.05 | 0.05 | 0.05 | 0.05 |
| Yellow #6/40 AC 7326 | 30.00 | 30.00 | 30.00 | 30.00 | 30.00 | 30.00 | 30.00 | 30.00 | 30.00 | 30.00 | 30.00 | 30.00 |
| Sodium Citrate | — | 0.05 | 0.10 | 0.15 | 0.20 | 0.50 | — | 0.05 | 0.10 | 0.15 | 0.20 | 0.50 |
| Total Percentage | 100 | 100 | 100 | 100 | 100 | 100 | 100 | 100 | 100 | 100 | 100 | 100 |
| Rating after 96 hrs. | 1.0* | 1.0* | 1.0* | 3.0* | 3.5 | 5.5 | 1.0* | 1.0* | 1.0* | 1.0* | 2.0* | 5.5 |
| Rating after 7 days | — | — | — | — | 3.0 | 5.0 | — | — | — | — | — | 5.0 |

| COMPONENTS | Trial 13 | 14 | 15 | 16 | 17 | 18 | 19 | 20 | 21 | 22 | 23 | 24 |
|---|---|---|---|---|---|---|---|---|---|---|---|---|
| Distilled Water | 69.90 | 69.85 | 69.80 | 69.75 | 69.70 | 69.40 | 69.50 | 69.45 | 69.40 | 69.35 | 69.30 | 69.00 |
| Gum Xanthan | 0.10 | 0.10 | 0.10 | 0.10 | 0.10 | 0.10 | 0.50 | 0.50 | 0.50 | 0.50 | 0.50 | 0.50 |
| Yellow #6/40 AC7326 | 30.00 | 30.00 | 30.00 | 30.00 | 30.00 | 30.00 | 30.00 | 30.00 | 30.00 | 30.00 | 30.00 | 30.00 |
| Sodium Citrate | — | 0.05 | 0.10 | 0.15 | 0.20 | 0.50 | — | 0.05 | 0.10 | 0.15 | 0.20 | 0.50 |

TABLE C-continued

| | Percentage Weight | | | | | | | | | | | |
|---|---|---|---|---|---|---|---|---|---|---|---|---|
| Total Percentage | 100 | 100 | 100 | 100 | 100 | 100 | 100 | 100 | 100 | 100 | 100 | 100 |
| Rating after 96 hrs. | 1.0 | 1.0 | 1.0 | 2.0 | 2.0 | 5.5 | 1.0 | 1.0 | 1.0 | 2.0 | 2.0 | 4.5 |
| Rating after 8 days | — | — | — | — | — | 5.0 | — | — | — | — | — | 5.0 |

*Denotes the sample was discarded after the 1st observation.

TABLE D

| | Percentage Weight | | | | | | | | | | | |
|---|---|---|---|---|---|---|---|---|---|---|---|---|
| | Trial | | | | | | | | | | | |
| COMPONENT | 1 | 2 | 3 | 4 | 5 | 6 | 7 | 8 | 9 | 10 | 11 | 12 |
| Distilled Water | 69.98 | 69.93 | 69.88 | 69.83 | 69.78 | 69.48 | 69.95 | 69.90 | 69.85 | 69.80 | 69.75 | 69.45 |
| Gum Xanthan | 0.02 | 0.02 | 0.02 | 0.02 | 0.02 | 0.02 | 0.05 | 0.05 | 0.05 | 0.05 | 0.05 | 0.05 |
| Yellow #6/40 AC 5617 | 30.00 | 30.00 | 30.00 | 30.00 | 30.00 | 30.00 | 30.00 | 30.00 | 30.00 | 30.00 | 30.00 | 30.00 |
| Sodium Citrate | — | 0.05 | 0.10 | 0.15 | 0.20 | 0.50 | — | 0.05 | 0.10 | 0.15 | 0.20 | 0.50 |
| Total Percentage | 100 | 100 | 100 | 100 | 100 | 100 | 100 | 100 | 100 | 100 | 100 | 100 |
| Rating after 96 hrs. | 1.0 | 1.0 | 1.0 | 1.0 | 2.0 | 4.0 | 1.0 | 1.0 | 1.0 | 1.0 | 2.0 | 5.0 |
| Rating after 7 days | — | — | — | — | — | 4.0 | — | — | — | — | — | 4.0 |
| | Trial | | | | | | | | | | | |
| COMPONENTS | 13 | 14 | 15 | 16 | 17 | 18 | 19 | 20 | 21 | 22 | 23 | 24 |
| Distilled Water | 69.90 | 69.85 | 69.80 | 69.75 | 69.70 | 69.40 | 69.50 | 69.45 | 69.40 | 69.35 | 69.30 | 69.00 |
| Gum Xanthan | 0.10 | 0.10 | 0.10 | 0.10 | 0.10 | 0.10 | 0.50 | 0.50 | 0.50 | 0.50 | 0.50 | 0.50 |
| Yellow #6/40 AC 5617 | 30.00 | 30.00 | 30.00 | 30.00 | 30.00 | 30.00 | 30.00 | 30.00 | 30.00 | 30.00 | 30.00 | 30.00 |
| Sodium Citrate | — | 0.05 | 0.10 | 0.15 | 0.20 | 0.50 | — | 0.05 | 0.10 | 0.15 | 0.20 | 0.50 |
| Total Percentage | 100 | 100 | 100 | 100 | 100 | 100 | 100 | 100 | 100 | 100 | 100 | 100 |
| Rating after 96 hrs. | 1.0* | 1.0 | 1.0 | 1.0 | 1.0 | 4.0 | 1.0 | 1.0 | 2.0 | 2.0 | 2.0 | 4.0 |
| Rating after 6 days | — | — | — | — | — | 4.0 | — | — | — | — | — | 4.0 |

*Denotes the sample was discarded after the 1st observation.

TABLE E

| | Percentage Weight | | | | | | | | | | | |
|---|---|---|---|---|---|---|---|---|---|---|---|---|
| | Trial | | | | | | | | | | | |
| COMPONENT | 1 | 2 | 3 | 4 | 5 | 6 | 7 | 8 | 9 | 10 | 11 | 12 |
| Distilled Water | 69.98 | 69.93 | 69.88 | 69.83 | 69.78 | 69.48 | 69.95 | 69.90 | 69.85 | 69.80 | 69.75 | 69.45 |
| Gum Xanthan | 0.02 | 0.02 | 0.02 | 0.02 | 0.02 | 0.02 | 0.05 | 0.05 | 0.05 | 0.05 | 0.05 | 0.05 |
| Blue #1/11% AC 5553 | 30.00 | 30.00 | 30.00 | 30.00 | 30.00 | 30.00 | 30.00 | 30.00 | 30.00 | 30.00 | 30.00 | 30.00 |
| Sodium Citrate | — | 0.05 | 0.10 | 0.15 | 0.20 | 0.50 | — | 0.05 | 0.10 | 0.15 | 0.20 | 0.50 |
| Total Percentage | 100 | 100 | 100 | 100 | 100 | 100 | 100 | 100 | 100 | 100 | 100 | 100 |
| Rating after 96 hrs. | 1.0 | 1.0 | 1.0 | 2.0 | 2.0 | 3.0 | 2.0 | 2.0 | 2.0 | 3.0 | 3.0 | 4.0 |
| Rating after 7 days | — | — | — | — | — | 2.0 | — | — | — | — | — | 3.0 |
| | Trial | | | | | | | | | | | |
| COMPONENT | 13 | 14 | 15 | 16 | 17 | 18 | 19 | 20 | 21 | 22 | 23 | 24 |
| Distilled Water | 69.90 | 69.85 | 69.80 | 69.75 | 69.70 | 69.40 | 69.50 | 69.45 | 69.40 | 69.35 | 69.30 | 69.00 |
| Gum Xanthan | 0.10 | 0.10 | 0.10 | 0.10 | 0.10 | 0.10 | 0.50 | 0.50 | 0.50 | 0.50 | 0.50 | 0.50 |
| Blue #1/11% AC5553 | 30.00 | 30.00 | 30.00 | 30.00 | 30.00 | 30.00 | 30.00 | 30.00 | 30.00 | 30.00 | 30.00 | 30.00 |
| Sodium Citrate | — | 0.05 | 0.10 | 0.15 | 0.20 | 0.50 | — | 0.05 | 0.10 | 0.15 | 0.20 | 0.50 |
| Total Percentage | 100 | 100 | 100 | 100 | 100 | 100 | 100 | 100 | 100 | 100 | 100 | 100 |
| Rating after 96 hrs. | 1.0 | 2.0 | 2.0 | 2.0 | 3.0 | 3.0 | 1.0 | 2.0 | 2.0 | 4.5 | 4.5 | 6.0 |
| Rating after 7 days | — | — | — | — | 3.0 | 3.0 | — | — | — | 3.0 | 4.0 | — |

TABLE F

| | Percentage Weight | | | | | | | | | | | |
|---|---|---|---|---|---|---|---|---|---|---|---|---|
| | Trial | | | | | | | | | | | |
| COMPONENT | 1 | 2 | 3 | 4 | 5 | 6 | 7 | 8 | 9 | 10 | 11 | 12 |
| Distilled Water | 69.98 | 69.93 | 69.88 | 69.83 | 69.78 | 69.48 | 69.95 | 69.90 | 69.85 | 69.80 | 69.75 | 69.45 |
| Gum Xanthan | 0.02 | 0.02 | 0.02 | 0.02 | 0.02 | 0.02 | 0.05 | 0.05 | 0.05 | 0.05 | 0.05 | 0.05 |
| Blue #1/11 AC 4934 | 30.00 | 30.00 | 30.00 | 30.00 | 30.00 | 30.00 | 30.00 | 30.00 | 30.00 | 30.00 | 30.00 | 30.00 |
| Sodium Citrate | — | 0.05 | 0.10 | 0.15 | 0.20 | 0.50 | — | 0.05 | 0.10 | 0.15 | 0.20 | 0.50 |
| Total Percentage | 100 | 100 | 100 | 100 | 100 | 100 | 100 | 100 | 100 | 100 | 100 | 100 |
| Rating after 96 hrs. | 1.0 | 1.0 | 1.0 | 1.0 | 1.0 | 1.0 | 1.0 | 1.0 | | 1.0 | 2.0 | 2.0 |
| Rating after 14 days | — | — | — | — | — | — | — | — | | — | — | — |
| | Trial | | | | | | | | | | | |
| COMPONENT | 13 | 14 | 15 | 16 | 17 | 18 | 19 | 20 | 21 | 22 | 23 | 24 |
| Distilled Water | 69.90 | 69.85 | 69.80 | 69.75 | 69.70 | 69.40 | 69.50 | 69.45 | 69.40 | 69.35 | 69.30 | 69.00 |
| Gum Xanthan | 0.10 | 0.10 | 0.10 | 0.10 | 0.10 | 0.10 | 0.50 | 0.50 | 0.50 | 0.50 | 0.50 | 0.50 |
| Blue #1/11 AC 4934 | 30.00 | 30.00 | 30.00 | 30.00 | 30.00 | 30.00 | 30.00 | 30.00 | 30.00 | 30.00 | 30.00 | 30.00 |
| Sodium Citrate | — | 0.05 | 0.10 | 0.15 | 0.20 | 0.50 | — | 0.05 | 0.10 | 0.15 | 0.20 | 0.50 |
| Total Percentage | 100 | 100 | 100 | 100 | 100 | 100 | 100 | 100 | 100 | 100 | 100 | 100 |

TABLE F-continued

| | Percentage Weight | | | | | | | | | | |
|---|---|---|---|---|---|---|---|---|---|---|---|
| Rating after 96 hrs. | 1.0 | 1.0 | 2.0 | 3.0 | 3.0 | 4.0 | 1.0 | 2.0 | 2.0 | 2.0 | 4.0 | 4.0 |
| Rating after 14 days | — | — | — | 2.0 | 2.0 | 3.5 | — | — | — | — | 2.0 | 3.0 |

TABLE G

Percentage Weight

| | Trial | | | | | | | | | | | |
|---|---|---|---|---|---|---|---|---|---|---|---|---|
| COMPONENT | 1 | 2 | 3 | 4 | 5 | 6 | 7 | 8 | 9 | 10 | 11 | 12 |
| Distilled Water | 69.98 | 69.93 | 69.88 | 69.83 | 69.78 | 69.48 | 69.95 | 69.90 | 69.85 | 69.80 | 69.75 | 69.45 |
| Gum Xanthan | 0.02 | 0.02 | 0.02 | 0.02 | 0.02 | 0.02 | 0.05 | 0.05 | 0.05 | 0.05 | 0.05 | 0.05 |
| Blue #2/39 AC5615 | 15.00 | 15.00 | 15.00 | 15.00 | 15.00 | 15.00 | 15.00 | 15.00 | 15.00 | 15.00 | 15.00 | 15.00 |
| TiO$_2$ 3328 | 15.00 | 15.00 | 15.00 | 15.00 | 15.00 | 15.00 | 15.00 | 15.00 | 15.00 | 15.00 | 15.00 | 15.00 |
| Sodium Citrate | — | 0.05 | 0.10 | 0.15 | 0.20 | 0.50 | — | 0.05 | 0.10 | 0.15 | 0.20 | 0.50 |
| Total Percentage | 100 | 100 | 100 | 100 | 100 | 100 | 100 | 100 | 100 | 100 | 100 | 100 |
| Rating after 96 hrs. | 1.0 | 2.0 | 2.0 | 3.0 | 3.0 | 3.5 | 1.0 | 3.0 | 3.0 | 3.5 | 3.5 | 4.0 |
| Rating after 11 days | — | — | — | 3.0 | 3.0 | 3.0 | — | 3.0 | 3.0 | 3.0 | 3.0 | 3.5 |

| | Trial | | | | | | | | | | | |
|---|---|---|---|---|---|---|---|---|---|---|---|---|
| COMPONENT | 13 | 14 | 15 | 16 | 17 | 18 | 19 | 20 | 21 | 22 | 23 | 24 |
| Distilled Water | 69.90 | 69.85 | 69.80 | 69.75 | 69.70 | 69.40 | 69.50 | 69.45 | 69.40 | 69.35 | 69.30 | 69.00 |
| Gum Xanthan | 0.10 | 0.10 | 0.10 | 0.10 | 0.10 | 0.10 | 0.50 | 0.50 | 0.50 | 0.50 | 0.50 | 0.50 |
| Blue #2/39 AC 5615 | 15.00 | 15.00 | 15.00 | 15.00 | 15.00 | 15.00 | 15.00 | 15.00 | 15.00 | 15.00 | 15.00 | 15.00 |
| TiO$_2$ 3328 | 15.00 | 15.00 | 15.00 | 15.00 | 15.00 | 15.00 | 15.00 | 15.00 | 15.00 | 15.00 | 15.00 | 15.00 |
| Sodium Citrate | — | 0.05 | 0.10 | 0.15 | 0.20 | 0.50 | — | 0.05 | 0.10 | 0.15 | 0.20 | 0.50 |
| Total Percentage | 100 | 100 | 100 | 100 | 100 | 100 | 100 | 100 | 100 | 100 | 100 | 100 |
| Rating after 96 hrs. | 1.0 | 1.0 | 1.0 | 2.0 | 2.0 | 3.0 | 1.0 | 1.0 | 1.0 | 1.0 | 2.0 | 2.0 |
| Rating after 11 days | — | — | — | 2.0 | 2.0 | 3.0 | — | — | — | — | — | — |

As is clear from Table A, in a combination of distilled water, gum xanthan, TiO$_2$, Yellow #6/40, and sodium citrate, it was found that with 0.10 percent gum, higher than the 0.02 of previous example 1, an optimal amount of sodium citrate is 0.15 percent. In Table A, this is represented by trial 2. When xanthan gum in the amount of 0.50 percent is added to the pigment suspension, as evidenced by trials 5 and 10, then the results are relatively poor, and it is apparent that the optimal amount of gum, regardless of the amount of sodium citrate, has been overreached.

In Table B, a different brand of lake has been tested, Yellow #6/40 AC 5617. It is apparent that the optimal composition contains gum in the amount of 0.02 to 0.10 percent weight and sodium citrate in the amount of 0.50 percent. This shows that the particular lake used will effect the precise optimal percentages of both gum and sodium citrate. The precise affect of a particular pigment is not predictable and must be determined empirically. It is desirable to determine, for each particular pigment, the optimal percent of each component by experiments such as shown in the above Tables. By varying the amount of gum while controlling the amount of sodium citrate, and vice-versa, optimal amounts can be determined. Such experimentation, in view of the guidelines and many examples given herein, can be readily determined by those of ordinary skill in the art.

The dependence of the properties of a suspension on the particular pigment employed is further evidenced by Table C. In the event that the pigment is not an equal mixture of Yellow #6/40 and titanium dioxide, but rather entirely Yellow #6/40, then new optimal percentages need to be ascertained. In table D, an optimal percent amount of sodium citrate appears to be 0.50, whether the gum is at 0.05, 0.10 or 0.20 percent. Higher amounts of gum, however, appear to give less satisfactory results regardless of the amount of sodium citrate.

Various blue dyes were tested. An equal mixture of Blue #1/11% and TiO$_2$ was tested. Blue #1/11% alone, wihout TiO$_2$, was also treated. The results are shown in Tables E and F. It is evident the optimal results were obtained with the percentages represented by trial 23 in Table F and trial 18 in Table F. For a pigment suspension containing about 70% distilled water, and 30% of an equal mixture of Blue #2/39 and TiO$_2$, optimal amounts of gum xanthan and sodium citrate were, respectively, 0.05 and 0.50, as shown in Table G.

In confectionary applications, a very good pigment suspension is achieved using a sugar solution as a solvent. The following is exemplary of a sugar based pigment suspension obtainable with all lakes:

EXAMPLE 6

The following components were weighted out and mixed:

| Component | Percent by Weight |
|---|---|
| Sugar solution | 58.80 |
| Sodium Citrate | 0.20 |
| Red #40/40% | 40.00 |

The sugar solution comprised a mixture of water and sucrose in a ratio of about 4:6. The resulting suspension exhibited excellent properties. The suspension was readily pourable and did not thicken over time.

It has also been found that the presence of a substantial amount of an organic solvent in the suspension eliminates the absolute need for a polymeric colloid, athough the results are generally not as good as with a polymeric colloid. The suspension apparently requires an effective amount of water which will dissolve the viscosity lowering agent and therefore, if desired, a small amount of water, for example, in an alcohol or propylene glycol based dispersion, is sufficient. Suspensions with 10% or less of water have worked satisfactorily. The following example illustrates a satisfactory pigment suspension.

EXAMPLE 7

The following components were weighted out and mixed:

| Component | Percent by Weight |
|---|---|
| Distilled Water | 49.80 |
| Propylene Glycol | 20.00 |
| Sodium Citrate | 0.20 |
| Yellow #6/40% | 30.00 |

This suspension exhibited satisfactory viscosity and non-settling properties. In place of propylene glycol, other organic solvents such as glycerin, polyethylene glycol, or the like may be employed. Pigments employed satisfactory included Yellow #6/17%, Blue #2/21%, Red #4/40%, Red #3/40%, and mixtures thereof with titanium dioxide.

The suspensions of the instant invention may also contain conventional preservatives in small amounts, in order to prevent the occurrence of mold, fungi, or other microbiological contaminants. For example, suitable preservatives approved for application in products intended for human consumption are potassium sorbate and methyl paraben. These preservatives may be employed in amounts less than 0.2 percent.

We claim:

1. A composition consisting essentially of a lake pigment, a polymeric colloid, said polymeric colloid being a natural or synthetic gum, a viscosity lowering agent, the viscosity lowering agent being a salt of a dicarboxylic or tricarboxylic acid compound, and an aqueous solvent, the aqueous solvent being water.

2. The composition of claim 1, wherein said gum is selected from the group consisting of gum arabic, quar gum, agar, xanthum gum, PG alginate, hydroxypropyl cellulose, gum trag, gelatin, pectin, and carrageenan.

3. The composition of claim 1, wherein said gum is selected from the group consisting of gum arabic, xanthan gum, and quar gum.

4. The composition of claim 1, wherein the pigment is an FD&C lake, D&C lake, or carmine.

5. The composition of claim 1, wherein the pigment is a combination of a lake pigment and titanium dioxide.

6. The composition of claim 1, wherein the viscosity lowering agent is the salt of an organic compound containing at least one carboxylic group.

7. The composition of claim 1, wherein the viscosity lowering agent is a lactone.

8. The composition of claim 1, wherein the viscosity lowering agent is selected from the group consisting of the salts of tartaric acid, citric acid, fumaric acid, adipic acid, maleic acid and ascorbic acid and mixtures with the acid form thereof.

9. The composition of claim 1, wherein the viscosity lowering agent is selected from the group consisting of salts of tartaric acid, citric acid and mixtures with the acid thereof.

10. The composition of claim 1, wherein the percent of the pigment is 20 to 75%, the percent of the polymeric colloid is 0.005 to 5, the percent of the viscosity lowering agent is 0.005 to 5 and the percent of an Aqueous solvent is 5 to 80.

11. The composition of claim 9, comprising 25 to 65% of a pigment, 0.01 to 2 percent of a gum, 0.005 to 2 percent of a viscosity lowering agent, and 10 to 75 percent of an aqueous solvent.

12. The composition of claim 9, comprising 30 to 60 percent of a pigment, 0.05 to 0.50 percent of a polymeric colloid, and 0.01 to 0.50 percent of a viscosity lowering agent, and 30 to 60 percent of an aqueous solvent.

13. A composition consisting essentially of a pigment, a viscosity lowering agent, the viscosity lowering agent being a salt of a dicarboxylic, or tricarboxylic acid compound, an aqueous solvent, the aqueous solvent being water, and an organic solvent.

14. The composition of claim 13, wherein the organic solvent is selected from the group comprising propylene glycol, glycerin, and polyethylene glycol.

15. A composition consisting essentially of a pigment, a viscosity lowering agent, the viscosity lowering agent being a salt of a dicarboxylic or tricarboxylic acid compound, sugar, and an aqueous solvent, the aqueous solvent being water.

16. The composition of claim 15, comprising by weight about 20 to 80 percent sugar syrup, about 25 to 65 percent pigment, and about 0.05 to 5 percent of a viscosity lowering agent.

17. The composition of claim 13, wherein the pigment is an FD&C lake, D&C lake, or carmine.

18. The composition of claim 13, wherein the pigment is a combination of a lake pigment and titanium dioxide.

19. The composition of claim 13, wherein the viscosity lowering agent is a lactone.

20. The composition of claim 13, wherein the viscosity lowering agent is selected form the group consisting of the salts of tartaric acid, citric acid, fumaric acid, adipic acid, maleic acid and ascorbic acid and mixtures with the acid thereof.

21. The composition of claim 15, wherein the viscosity lowering agent is in the range of 0.1 to 1.0 percent, preferably 0.5.

22. The composition of claim 15, wherein the sugar is sucrose.

23. The composition of claim 15, wherein the viscosity lowering agent is selected from the group consisting of salts of tartaric acid, citric acid and mixtures of the acid thereof.

* * * * *